(12) United States Patent
Liran et al.

(10) Patent No.: US 9,192,464 B2
(45) Date of Patent: Nov. 24, 2015

(54) RETINAL PROSTHESIS WITH EFFICIENT PROCESSING CIRCUITS

(71) Applicant: NANO-RETINA, INC., Wilmington, DE (US)

(72) Inventors: Tuvia Liran, Qiryat Tivon (IL); Ra'anan Gefen, Re'ut (IL)

(73) Assignee: NANO-RETINA, INC., Wilmington, DE (US)

(*) Notice: Subject to any disclaimer, the term of this patent is extended or adjusted under 35 U.S.C. 154(b) by 151 days.

(21) Appl. No.: 14/018,850

(22) Filed: Sep. 5, 2013

(65) Prior Publication Data
US 2014/0031931 A1   Jan. 30, 2014

Related U.S. Application Data

(63) Continuation of application No. 13/034,516, filed on Feb. 24, 2011, now Pat. No. 8,571,669.

(51) Int. Cl.
*A61F 2/14* (2006.01)
*A61N 1/36* (2006.01)

(52) U.S. Cl.
CPC ............ *A61F 2/14* (2013.01); *A61N 1/36046* (2013.01)

(58) Field of Classification Search
CPC .... A61N 1/36046; A61N 1/0543; A61F 2/14; A61F 9/08
See application file for complete search history.

(56) References Cited

U.S. PATENT DOCUMENTS

| | | | |
|---|---|---|---|
| 1,662,446 A | 3/1928 | Wappler | |
| 2,721,316 A | 10/1955 | Shaw | |
| 2,760,483 A | 8/1956 | Graham | |
| 4,197,850 A | 4/1980 | Schulman et al. | |
| 4,262,294 A * | 4/1981 | Hara et al. | 347/144 |
| 4,272,910 A | 6/1981 | Danz | |
| 4,324,252 A | 4/1982 | Rossing et al. | |
| 4,486,861 A | 12/1984 | Harmel | |
| 4,551,149 A | 11/1985 | Sciarra | |
| 4,601,545 A | 7/1986 | Kern | |
| 4,628,933 A * | 12/1986 | Michelson | 607/53 |
| 4,664,117 A | 5/1987 | Beck | |

(Continued)

FOREIGN PATENT DOCUMENTS

| CA | 2235216 A1 | 4/1997 |
|---|---|---|
| CA | 2235316 | 4/1997 |

(Continued)

OTHER PUBLICATIONS

ISR and written opinion, dated Feb. 27, 2014, which issued in PCT/IB2013/060270.

(Continued)

*Primary Examiner* — Catherine Voorhees
(74) *Attorney, Agent, or Firm* — Symbus Law Group, LLC; Clifford D. Hyra

(57) ABSTRACT

A medical device includes an array of electrodes, configured for implantation in contact with tissue in an eye of a living subject. Driver circuitry is configured to drive the electrodes in an alternating pattern, such that different groups of the electrodes are driven to stimulate the tissue during different, predetermined respective time periods. A power sensor, may be coupled to deactivate a first group of the electrodes when the available electrical power drops below a predetermined threshold, while a second group of the electrodes remains active. Other embodiments are also described.

1 Claim, 9 Drawing Sheets

(56) References Cited

U.S. PATENT DOCUMENTS

| | | |
|---|---|---|
| 4,786,818 A | 11/1988 | Mead et al. |
| 4,837,049 A | 6/1989 | Byers et al. |
| 4,903,702 A | 2/1990 | Putz |
| 4,914,738 A | 4/1990 | Oda et al. |
| 4,969,468 A | 11/1990 | Byers et al. |
| 5,016,633 A | 5/1991 | Chow |
| 5,024,223 A | 6/1991 | Chow |
| 5,081,378 A | 1/1992 | Watanabe |
| 5,108,427 A | 4/1992 | Majercik et al. |
| 5,109,844 A | 5/1992 | de Juan, Jr. et al. |
| 5,133,356 A | 7/1992 | Bryan et al. |
| 5,147,284 A | 9/1992 | Fedorov et al. |
| 5,159,927 A | 11/1992 | Schmid |
| 5,215,088 A | 6/1993 | Normann et al. |
| 5,313,642 A | 5/1994 | Seigel |
| 5,314,458 A | 5/1994 | Najafi et al. |
| 5,397,350 A | 3/1995 | Chow et al. |
| 5,411,540 A | 5/1995 | Edell et al. |
| 5,476,494 A | 12/1995 | Edell et al. |
| 5,526,423 A | 6/1996 | Ohuchi et al. |
| 5,575,813 A | 11/1996 | Edell et al. |
| 5,597,381 A | 1/1997 | Rizzo, III |
| 5,608,204 A | 3/1997 | Hofflinger et al. |
| 5,665,954 A | 9/1997 | Bard et al. |
| 5,674,263 A | 10/1997 | Yamamoto et al. |
| 5,735,882 A | 4/1998 | Rottenberg et al. |
| 5,769,875 A | 6/1998 | Peckham et al. |
| 5,800,478 A | 9/1998 | Chen et al. |
| 5,800,533 A | 9/1998 | Eggleston et al. |
| 5,800,535 A | 9/1998 | Howard, III |
| 5,835,250 A | 11/1998 | Kanesaka |
| 5,836,996 A | 11/1998 | Doorish |
| 5,837,995 A | 11/1998 | Chow et al. |
| 5,850,514 A | 12/1998 | Gonda et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 5,949,064 A | 9/1999 | Chow et al. |
| 6,020,593 A | 2/2000 | Chow et al. |
| 6,032,062 A | 2/2000 | Nisch |
| 6,035,236 A * | 3/2000 | Jarding et al. ............... 607/53 |
| 6,043,437 A | 3/2000 | Schulman et al. |
| 6,069,365 A | 5/2000 | Chow et al. |
| 6,075,251 A | 6/2000 | Chow et al. |
| 6,201,234 B1 | 3/2001 | Chow et al. |
| 6,230,057 B1 | 5/2001 | Chow et al. |
| 6,259,937 B1 | 7/2001 | Schulman et al. |
| 6,287,372 B1 | 9/2001 | Briand et al. |
| 6,298,270 B1 | 10/2001 | Nisch et al. |
| 6,324,429 B1 | 11/2001 | Shire et al. |
| 6,347,250 B1 | 2/2002 | Nisch et al. |
| 6,368,349 B1 | 4/2002 | Wyatt et al. |
| 6,389,317 B1 | 5/2002 | Chow et al. |
| 6,400,989 B1 | 6/2002 | Eckmiller |
| 6,427,087 B1 | 7/2002 | Chow et al. |
| 6,442,431 B1 | 8/2002 | Veraart et al. |
| 6,450,816 B1 | 9/2002 | Gerber |
| 6,458,157 B1 | 10/2002 | Suaning |
| 6,472,122 B1 | 10/2002 | Schulman et al. |
| 6,473,365 B2 | 10/2002 | Joh et al. |
| 6,498,043 B1 | 12/2002 | Schulman et al. |
| 6,507,758 B1 | 1/2003 | Greenberg et al. |
| 6,533,798 B2 | 3/2003 | Greenberg et al. |
| 6,574,022 B2 | 6/2003 | Chow et al. |
| 6,611,716 B2 | 8/2003 | Chow et al. |
| 6,647,297 B2 | 11/2003 | Scribner |
| 6,658,299 B1 | 12/2003 | Dobelle |
| 6,677,225 B1 | 1/2004 | Ellis et al. |
| 6,678,458 B2 | 1/2004 | Ellis et al. |
| 6,683,645 B1 | 1/2004 | Collins et al. |
| 6,738,672 B2 | 5/2004 | Schulman et al. |
| 6,755,530 B1 | 6/2004 | Loftus et al. |
| 6,758,823 B2 | 7/2004 | Pasquale et al. |
| 6,761,724 B1 | 7/2004 | Zrenner et al. |
| 6,762,116 B1 | 7/2004 | Skidmore |
| 6,770,521 B2 | 8/2004 | Visokay et al. |
| 6,785,303 B1 | 8/2004 | Holzwarth et al. |
| 6,792,314 B2 | 9/2004 | Byers et al. |
| 6,804,560 B2 | 10/2004 | Nisch et al. |
| 6,821,154 B1 | 11/2004 | Canfield et al. |
| 6,844,023 B2 | 1/2005 | Schulman et al. |
| 6,847,847 B2 | 1/2005 | Nisch et al. |
| 6,888,571 B1 | 5/2005 | Koshizuka et al. |
| 6,904,239 B2 | 6/2005 | Chow et al. |
| 6,908,470 B2 | 6/2005 | Stieglitz et al. |
| 6,923,669 B1 | 8/2005 | Tsui et al. |
| 6,935,897 B2 | 8/2005 | Canfield et al. |
| 6,949,763 B2 | 9/2005 | Ovadia et al. |
| 6,961,619 B2 | 11/2005 | Casey |
| 6,970,745 B2 | 11/2005 | Scribner |
| 6,974,533 B2 | 12/2005 | Zhou |
| 6,976,998 B2 * | 12/2005 | Rizzo et al. ............... 623/6.63 |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,025,619 B2 | 4/2006 | Tsui et al. |
| 7,027,874 B1 | 4/2006 | Sawan et al. |
| 7,031,776 B2 | 4/2006 | Chow et al. |
| 7,035,692 B1 | 4/2006 | Maghribi et al. |
| 7,037,943 B2 | 5/2006 | Peyman |
| 7,047,080 B2 | 5/2006 | Palanker et al. |
| 7,058,455 B2 | 6/2006 | Huie, Jr. et al. |
| 7,071,546 B2 | 7/2006 | Fey et al. |
| 7,079,881 B2 | 7/2006 | Schulman et al. |
| 7,081,630 B2 | 7/2006 | Saini et al. |
| 7,096,568 B1 | 8/2006 | Nilsen et al. |
| 7,103,416 B2 | 9/2006 | Ok et al. |
| 7,107,097 B2 | 9/2006 | Stern et al. |
| 7,127,286 B2 | 10/2006 | Mech et al. |
| 7,127,301 B1 | 10/2006 | Okandan et al. |
| 7,130,693 B1 | 10/2006 | Montalbo |
| 7,133,724 B2 | 11/2006 | Greenberg et al. |
| 7,139,612 B2 | 11/2006 | Chow et al. |
| 7,147,865 B2 | 12/2006 | Fishman et al. |
| 7,149,586 B2 | 12/2006 | Greenberg et al. |
| 7,158,834 B2 | 1/2007 | Paul, Jr. |
| 7,158,836 B2 | 1/2007 | Suzuki |
| 7,160,672 B2 | 1/2007 | Schulman et al. |
| 7,162,308 B2 | 1/2007 | O'Brien et al. |
| 7,177,697 B2 | 2/2007 | Eckmiller et al. |
| 7,190,051 B2 | 3/2007 | Mech et al. |
| 7,191,010 B2 | 3/2007 | Ohta et al. |
| 7,224,300 B2 | 5/2007 | Dai et al. |
| 7,224,301 B2 | 5/2007 | Dai et al. |
| 7,235,350 B2 | 6/2007 | Schulman et al. |
| 7,242,597 B2 | 7/2007 | Shodo |
| 7,244,027 B2 | 7/2007 | Sumiya |
| 7,248,928 B2 | 7/2007 | Yagi |
| 7,251,528 B2 | 7/2007 | Harold |
| 7,255,871 B2 | 8/2007 | Huie, Jr. et al. |
| 7,257,446 B2 | 8/2007 | Greenberg et al. |
| 7,263,403 B2 | 8/2007 | Greenberg et al. |
| 7,271,525 B2 | 9/2007 | Byers et al. |
| 7,272,447 B2 | 9/2007 | Stett et al. |
| 7,291,540 B2 | 11/2007 | Mech et al. |
| 7,295,872 B2 | 11/2007 | Kelly et al. |
| 7,302,598 B2 | 11/2007 | Suzuki et al. |
| 7,314,474 B1 | 1/2008 | Greenberg et al. |
| 7,321,796 B2 | 1/2008 | Fink et al. |
| 7,342,427 B1 | 3/2008 | Fensore et al. |
| 7,377,646 B2 | 5/2008 | Suzuki |
| 7,379,000 B2 | 5/2008 | Dai et al. |
| 7,388,288 B2 | 6/2008 | Solzbacher et al. |
| 7,400,021 B2 | 7/2008 | Wu et al. |
| 7,447,547 B2 | 11/2008 | Palanker |
| 7,447,548 B2 | 11/2008 | Eckmiller |
| 7,480,988 B2 | 1/2009 | Ok et al. |
| 7,481,912 B2 | 1/2009 | Stelzle et al. |
| 7,482,957 B2 | 1/2009 | Dai et al. |
| 7,483,751 B2 | 1/2009 | Greenberg et al. |
| 7,493,169 B2 | 2/2009 | Greenberg et al. |

(56) References Cited

U.S. PATENT DOCUMENTS

| | | | |
|---|---|---|---|
| 7,499,754 B2 | 3/2009 | Greenberg et al. |
| 7,539,544 B2 | 5/2009 | Greenberg et al. |
| 7,555,328 B2 | 6/2009 | Schulman et al. |
| 7,556,621 B2 | 7/2009 | Palanker et al. |
| 7,565,202 B2 | 7/2009 | Greenberg et al. |
| 7,565,203 B2 | 7/2009 | Greenberg et al. |
| 7,571,004 B2 | 8/2009 | Roy et al. |
| 7,571,011 B2 | 8/2009 | Zhou et al. |
| 7,574,263 B2 | 8/2009 | Greenberg et al. |
| 7,610,098 B2 | 10/2009 | McLean |
| 7,622,702 B2 | 11/2009 | Wu et al. |
| 7,630,771 B2 | 12/2009 | Cauller |
| 7,631,424 B2 | 12/2009 | Greenberg et al. |
| 7,638,032 B2 | 12/2009 | Zhou et al. |
| 7,666,523 B2 | 2/2010 | Zhou |
| 7,676,274 B2 | 3/2010 | Hung et al. |
| 7,691,252 B2 | 4/2010 | Zhou et al. |
| 7,706,887 B2 | 4/2010 | Tai et al. |
| 7,706,893 B2 | 4/2010 | Hung et al. |
| 7,709,961 B2 | 5/2010 | Greenberg et al. |
| 7,725,191 B2 | 5/2010 | Greenberg et al. |
| 7,734,352 B2 | 6/2010 | Greenberg et al. |
| 7,738,962 B2 | 6/2010 | Greenberg et al. |
| 7,749,608 B2 | 7/2010 | Laude et al. |
| 7,750,076 B2 | 7/2010 | Laude et al. |
| 7,751,896 B2 | 7/2010 | Graf et al. |
| 7,765,009 B2 | 7/2010 | Greenberg et al. |
| 7,766,903 B2 | 8/2010 | Blumenkranz et al. |
| 7,776,197 B2 | 8/2010 | Zhou |
| 7,831,309 B1 * | 11/2010 | Humayun et al. ............... 607/54 |
| 7,834,767 B2 | 11/2010 | Shodo |
| 7,835,798 B2 | 11/2010 | Greenberg et al. |
| 7,840,273 B2 | 11/2010 | Schmid |
| 7,846,285 B2 | 12/2010 | Zhou et al. |
| 7,853,330 B2 | 12/2010 | Bradley et al. |
| 7,871,707 B2 | 1/2011 | Laude et al. |
| 7,877,866 B1 | 2/2011 | Greenberg et al. |
| 7,881,799 B2 | 2/2011 | Greenberg et al. |
| 7,887,681 B2 | 2/2011 | Zhou |
| 7,894,909 B2 | 2/2011 | Greenberg et al. |
| 7,894,911 B2 | 2/2011 | Greenberg et al. |
| 7,904,148 B2 | 3/2011 | Greenberg et al. |
| 7,908,011 B2 | 3/2011 | McMahon et al. |
| 7,912,556 B2 | 3/2011 | Greenberg et al. |
| 7,914,842 B1 | 3/2011 | Greenberg et al. |
| 7,937,153 B2 | 5/2011 | Zhou et al. |
| 7,957,811 B2 | 6/2011 | Caspi et al. |
| 7,962,221 B2 | 6/2011 | Greenberg et al. |
| 7,979,134 B2 | 7/2011 | Chow et al. |
| 7,983,308 B1 | 7/2011 | Johnston et al. |
| 7,989,080 B2 | 8/2011 | Greenberg et al. |
| 8,000,804 B1 | 8/2011 | Wessendorf et al. |
| 8,010,202 B2 | 8/2011 | Shah et al. |
| 8,010,206 B2 | 8/2011 | Dai et al. |
| 8,014,868 B2 | 9/2011 | Greenberg et al. |
| 8,014,869 B2 | 9/2011 | Greenberg et al. |
| 8,014,878 B2 | 9/2011 | Greenberg et al. |
| 8,024,022 B2 | 9/2011 | Schulman et al. |
| 8,034,229 B2 | 10/2011 | Zhou et al. |
| 8,046,078 B2 | 10/2011 | Greenberg et al. |
| 8,060,211 B2 | 11/2011 | Greenberg et al. |
| 8,060,216 B2 | 11/2011 | Greenberg et al. |
| 8,068,913 B2 | 11/2011 | Greenberg et al. |
| 8,078,284 B2 | 12/2011 | Greenberg et al. |
| 8,090,447 B2 | 1/2012 | Tano et al. |
| 8,090,448 B2 | 1/2012 | Greenberg et al. |
| 8,103,352 B2 | 1/2012 | Fried et al. |
| 8,121,697 B2 | 2/2012 | Greenberg et al. |
| 8,131,375 B2 | 3/2012 | Greenberg et al. |
| 8,131,378 B2 | 3/2012 | Greenberg et al. |
| 8,145,322 B1 | 3/2012 | Yao et al. |
| 8,150,526 B2 | 4/2012 | Gross et al. |
| 8,150,534 B2 | 4/2012 | Greenberg et al. |
| 8,160,713 B2 | 4/2012 | Greenberg et al. |
| 8,165,680 B2 | 4/2012 | Greenberg et al. |
| 8,170,676 B2 | 5/2012 | Greenberg et al. |
| 8,170,682 B2 | 5/2012 | Greenberg et al. |
| 8,180,453 B2 | 5/2012 | Greenberg et al. |
| 8,180,454 B2 | 5/2012 | Greenberg et al. |
| 8,180,460 B2 | 5/2012 | Nevsmith et al. |
| 8,190,267 B2 | 5/2012 | Greenberg et al. |
| 8,195,266 B2 | 6/2012 | Whalen, III et al. |
| 8,197,539 B2 | 6/2012 | Nasiatka et al. |
| 8,200,338 B2 | 6/2012 | Grennberg et al. |
| 8,226,661 B2 | 7/2012 | Balling et al. |
| 8,239,034 B2 | 8/2012 | Greenberg et al. |
| 8,244,362 B2 | 8/2012 | Yonezawa |
| 8,249,716 B2 | 8/2012 | Tano et al. |
| 8,567,048 B2 | 10/2013 | Singh et al. |
| 2001/0011844 A1 | 8/2001 | Ernst et al. |
| 2002/0091421 A1 | 7/2002 | Greenberg et al. |
| 2002/0173889 A1 | 11/2002 | Odinak et al. |
| 2003/0023297 A1 | 1/2003 | Byers et al. |
| 2003/0032946 A1 | 2/2003 | Fishman et al. |
| 2003/0110508 A1 | 6/2003 | Bridgelall |
| 2003/0132946 A1 | 7/2003 | Gold |
| 2003/0181957 A1 | 9/2003 | Greenberg |
| 2004/0054407 A1 | 3/2004 | Tashiro et al. |
| 2004/0078064 A1 | 4/2004 | Suzuki |
| 2004/0082981 A1 | 4/2004 | Chow et al. |
| 2004/0088026 A1 | 5/2004 | Chow et al. |
| 2004/0098067 A1 | 5/2004 | Ohta et al. |
| 2004/0181265 A1 | 9/2004 | Palanker et al. |
| 2004/0189940 A1 | 9/2004 | Kutschbach et al. |
| 2005/0015120 A1 | 1/2005 | Seibel et al. |
| 2005/0119605 A1 | 6/2005 | Sohn |
| 2005/0146954 A1 | 7/2005 | Win et al. |
| 2005/0168569 A1 | 8/2005 | Igarashi |
| 2006/0106432 A1 | 5/2006 | Sawan et al. |
| 2006/0111757 A9 | 5/2006 | Greenberg et al. |
| 2006/0184245 A1 | 8/2006 | Graf et al. |
| 2006/0256989 A1 | 11/2006 | Olsen et al. |
| 2006/0282128 A1 | 12/2006 | Tai et al. |
| 2006/0287688 A1 | 12/2006 | Yonezawa |
| 2007/0005116 A1 | 1/2007 | Lo |
| 2007/0123766 A1 | 5/2007 | Whalen et al. |
| 2007/0142877 A1 | 6/2007 | McLean |
| 2007/0142878 A1 | 6/2007 | Krulevitch et al. |
| 2007/0191909 A1 | 8/2007 | Ameri et al. |
| 2008/0114230 A1 | 5/2008 | Addis |
| 2008/0234791 A1 | 9/2008 | Arle et al. |
| 2008/0262571 A1 | 10/2008 | Greenberg et al. |
| 2008/0288036 A1 | 11/2008 | Greenberg et al. |
| 2008/0294224 A1 | 11/2008 | Greenberg |
| 2009/0002034 A1 | 1/2009 | Westendorp et al. |
| 2009/0005835 A1 | 1/2009 | Greenberg et al. |
| 2009/0024182 A1 | 1/2009 | Zhang et al. |
| 2009/0118805 A1 | 5/2009 | Greenberg et al. |
| 2009/0192571 A1 | 7/2009 | Stett et al. |
| 2009/0204207 A1 | 8/2009 | Blum et al. |
| 2009/0204212 A1 | 8/2009 | Greenberg et al. |
| 2009/0216295 A1 | 8/2009 | Zrenner et al. |
| 2009/0228069 A1 | 9/2009 | Dai et al. |
| 2009/0287275 A1 | 11/2009 | Suaning et al. |
| 2009/0326623 A1 | 12/2009 | Greenberg et al. |
| 2010/0087895 A1 * | 4/2010 | Zhou et al. ...................... 607/54 |
| 2010/0174224 A1 | 7/2010 | Sohn |
| 2010/0204754 A1 | 8/2010 | Gross |
| 2010/0249878 A1 | 9/2010 | McMahon et al. |
| 2010/0331682 A1 | 12/2010 | Stein et al. |
| 2011/0054583 A1 | 3/2011 | Litt et al. |
| 2011/0172736 A1 | 7/2011 | Gefen et al. |
| 2011/0254661 A1 | 10/2011 | Fawcett et al. |
| 2012/0035725 A1 | 2/2012 | Gefen et al. |
| 2012/0035726 A1 | 2/2012 | Gross |
| 2012/0041514 A1 | 2/2012 | Gross et al. |
| 2012/0194781 A1 | 8/2012 | Agurok |
| 2012/0209350 A1 | 8/2012 | Taylor et al. |
| 2012/0221103 A1 | 8/2012 | Liran et al. |
| 2012/0259410 A1 | 10/2012 | Gefen et al. |
| 2012/0268080 A1 | 10/2012 | Jeon et al. |
| 2012/0269205 A1 | 10/2012 | Haque et al. |
| 2012/0283800 A1 | 11/2012 | Perryman et al. |

(56) References Cited

U.S. PATENT DOCUMENTS

| | | | |
|---|---|---|---|
| 2013/0126713 | A1 | 5/2013 | Haas et al. |
| 2013/0322462 | A1 | 12/2013 | Poulsen |
| 2014/0047713 | A1 | 2/2014 | Singh et al. |

FOREIGN PATENT DOCUMENTS

| | | |
|---|---|---|
| CN | 2650300 | 10/2004 |
| CN | 1875895 | 12/2006 |
| DE | 10315397 | 10/2004 |
| DE | 10315397 A1 | 10/2004 |
| JP | 2000-350742 | 12/2000 |
| JP | 2007042569 | 2/2007 |
| WO | WO0174444 | 10/2001 |
| WO | 0191854 A1 | 12/2001 |
| WO | 03032946 A2 | 4/2003 |
| WO | 2007009539 A2 | 1/2007 |
| WO | WO 2007/076347 | 5/2007 |
| WO | 2007/095395 A2 | 8/2007 |
| WO | 2010/035173 A1 | 4/2010 |
| WO | 2010089739 A2 | 8/2010 |
| WO | 2011/086545 A2 | 7/2011 |
| WO | 2012/017426 A1 | 2/2012 |
| WO | 2012/114327 A2 | 8/2012 |
| WO | WO 2012/114327 | 8/2012 |
| WO | 2012/153325 A2 | 11/2012 |

OTHER PUBLICATIONS

Examination Report, dated Apr. 16, 2014, which issued during prosecution of EP11732733.8.
Official Action, dated Nov. 27, 2013, which issued during prosecution of JP 2011-548843.
Examination Report, dated Feb. 26, 2014, which issued during prosecution of EP10738277.2.
Extended European Search Report, dated Nov. 19, 2013, which issued during the prosecution of European Patent Application No. 11814197.7.
J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.
A Restriction Requirement dated Jul. 18, 2012, which issued during the prosecution of U.S. Appl. No. 13/034,516.
An Office Action dated Dec. 14, 2012, which issued during the prosecution of U.S. Appl. No. 13/034,516.
A Notice of Allowance together with the Examiner initiated Interview Summary both dated Jun. 26, 2013 which issued during the prosecution of U.S. Appl. No. 13/034,516.
Jourdain R P., et al., "Fabrication of piezoelectric thick-film bimorph micro-actuators from bulk ceramics using batch-scale methods" Multi-Material Micro Manufacture, S. Dimov and W. Menz (Eds.) 2008 Cardiff University, Cardiff, UK., Whittles Publishing Ltd.
Lianga C, et al., "Surface modification of cp-Ti using femtosecond laser micromachining and the deposition of Ca/P layer" Materials Letters vol. 62, Issue 23, Aug. 31, 2008, pp. 3783-3786.
Seo J M., et al., "Biocompatibility of polyimide microelectrode array for retinal stimulation," Materials Science and Engineering: C, vol. 24, No. 1, Jan. 5, 2004, pp. 185-189 (5).
Sorkin R., et al., "Process entanglement as a neuronal anchorage mechanism to rough surfaces," Nanotechnology 20 (2009) 015101 (8pp).
Vorobyeva A Y. et al., "Metallic light absorbers produced by femtosecond laser pulses," Advances in Mechanical Engineering vol. 2010, Article ID 452749, 4 pages doi:10.1155/2010/452749, Hindawi Publishing Corporation.
Vorobyeva A Y. et al., "Femtosecond laser structuring of titanium implants," Applied Surface Science vol. 253, Issue 17, Jun. 30, 2007, pp. 7272-7280.
Wallman L., et al., "The geometric design of micromachined silicon sieve electrodes influences functional nerve regeneration," Biomaterials May 2001:22(10):1187-93.

Warren M. Grill, et al. "Implanted Neural Interfaces: Biochallenges and Engineered Solutions", Annu. Rev. Biomed. Eng. 2009, 11:1-24.
International Search Report dated Aug. 17, 2010 in connection with PCT/IL2010/00097.
Puech M., et al., "Fabrication of 3D packaging TSV using DRIE" Alcatel Micro Machining Systems, www.adixen.com.
Stein DJ, et al., "High voltage with Si series photovoltaics" Proceedings of SPIE, the International Society for Optical Engineering 2006, vol. 6287, pp. 62870D.1-62870D.
Starzyk JA, et al., "A DC-DC charge pump design based on voltage doublers" IEEE Transaction on Circuits and Systems-I: Fundamental theory and applications, vol. 48, No. 3, Mar. 2001.
Walter P., et al., "Cortical Activation via an implanted wireless retinal prosthesis," Investigative Ophthalmology and Visual Science. 2005;46:1780-1785.
Wu J T. and Chang K L., "MOS charge pumps for low-voltage operation" IEEE Journal of Solid-State Circuits, vol. 33 No. 4 Apr. 1998.
Swain P K., et al., "Back-Illuminated Image Sensors Come to the Forefront. Novel materials and fabrication methods increase quality and lower cost of sensors for machine vision and industrial imaging." Photonics Spectra Aug. 2008.
Sony Global News Release "Sony develops back-illuminated CMOS image sensor, realizing high picture quality, nearly twofold sensitivity (*1) and low noise," published Feb. 24, 2011 at "<http://www.sony.net/SonyInfo/News/Press/200806/08-069E/index.html>", pp. 1-3.
David C Ng, et al., "Pulse frequency modulation based CMOS image sensor for subretinal stimulation" IEEE Transactions on Circuits and Systems-II: Express Briefs, vol. 53, No. 6, Jun. 2006.
Kim B., "Through-Silicon-Via Copper Deposition for Vertical Chip Integration" Master. Res. Soc. Symp. Proc. vol. 970, 2007 Material Research Society.
Delbruck and Mead, "Analog VLSI Adptive, Logarithmic, Wide-dynamic-Range Photoreceptor," 1994 International Symposium on Circuits and Systems (London, 1994), pp. 339-342.
International Search Report dated Aug. 12, 2011 for Application No. PCT/IL2011/00022.
Written Opinion dated Aug. 12, 2011 for Application No. PCT/IL2011/00022.
Office Acrion issued Aug. 24, 2011 for Applicant's U.S. Appl. No. 12/368,150.
International Search Report and Written Opinion issed Dec. 12, 2011 in connection with PCT/IL2011-00609.
Palanker D. et al., "Design of a high-resolution optoelectric retinal prosthesis". Journal of Neural Engineering, Institute of physics publishing, Bristol, GB. vol. 2, No. 1, Mar. 1, 2005, pp. S105-S120, XP002427333, ISSN: 1741-2552, DOI: 10.1088/1741-2560/2/1/012.
Supplementary European Search Report dated Aug. 10, 2012, which issued during the prosecution of Applicant's European Application No. 10 73 8277.
International Preliminary Report on Patentability dated Jul. 17, 2012, which issued during the prosecution of Applicant's PCT/IL2011/000022.
Schwarz et al.: "Single-Chip CMOS Image Sensors for a Retina Implant System", Member, IEEE, 2000.
Pelayo et al.: "Cortical Visual Neuro-Prosthesis for the Blind: Retina-Like Software/Hardware Preprocessor", Dept. of Computer Architecture and Technology, University of Granada, Spain, Neural Engineering, 2003. Conference Proceedings. First International IEEE EMBS Conference.
An Office Action dated Sep. 28, 2012, which issued during the prosecution of U.S. Appl. No. 13/103,264.
International Search Report and a Written Opinion both dated Sep. 17, 2012, which issued during the prosecution of Applicant's PCT/IL12/00057.
Office Action dated Aug. 28, 2012, which issued during the prosecution of U.S. Appl. No. 12/852,218.
M. Schwarz, et al.. "Hardware Architecture of a Neural Net Based Retina Implant for Patients Suffereing from Retinitis Pigmentosa", Fraunhofer Institute of Microelectric Circuits and Systems, 1996, pp. 653-658.

(56) References Cited

OTHER PUBLICATIONS

K. Ganesan, et al. "Diamond Penetrating Electrode Array for Epi-Retinal Prosthesis," 32nd Annual International Conference of the IEEE EMBS, Buenos Aires, Argentina, Aug. 31-Sep. 4, 2010, pp. 6757-6760.
W. Finn, et al., "An Amphibian Model for Developing and Evaluating Retinal Protheses," 18th Annual International Conference of the IEEE Engineering in Medicine and Biology Society, Amsterdam 1996, pp. 1540-1541.
Shawn Kelly, "A system for electrical Retinal Stimulation for Human Trials", Massachusetts Institute of Technology, Jun. 1998, pp. 1-45.
A. Andreaou, et al., "Translinear Circuits in Subthreshold MOS," Analog Integrated Circuits and Signal Processing, Vol. , pp. 141-166 (1996).
Zrenner E., "Will Retinal Implants Restore Vision?" Science 295(5557), 2002, pp. 1022-1025.
Partial International Search Report Dated Mar. 31, 2015 (previously submitted).
Partial International Search Report dated Mar. 24, 2015 (previously submitted).
Office action that issued on Feb. 5, 2015 in U.S. Appl. No. 14/199,462.
Office action that issued on Mar. 3, 2015 in U.S. Appl. No. 13/148,461.
Office action that issued on Feb. 3, 2014 in U.S. Appl. No. 13/683,158.
EP search report dated Feb. 20, 2015 that issued in EP 12782462.1.
The ISR and the Written Opinion issued on Jun. 30, 2015 in PCT/IB2014/067417.
The ISR and the Written Opinion issued on Jun. 30, 2015 in PCT/IB2015/050224.
The office action as issued in U.S. Appl. No. 14/160,314 on Aug. 20, 2015.

* cited by examiner

| 0 | 4 | 1 | 5 | 0 | 4 | 1 | 5 | 0 | 4 | 1 | 5 |
|---|---|---|---|---|---|---|---|---|---|---|---|
| 12 | 8 | 13 | 9 | 12 | 8 | 13 | 9 | 12 | 8 | 13 | 9 |
| 2 | 6 | 3 | 7 | 2 | 6 | 3 | 7 | 2 | 6 | 3 | 7 |
| 14 | 10 | 15 | 11 | 14 | 10 | 15 | 11 | 14 | 10 | 15 | 11 |
| 0 | 4 | 1 | 5 | 0 | 4 | 1 | 5 | 0 | 4 | 1 | 5 |
| 12 | 8 | 13 | 9 | 12 | 8 | 13 | 9 | 12 | 8 | 13 | 9 |
| 2 | 6 | 3 | 7 | 2 | 6 | 3 | 7 | 2 | 6 | 3 | 7 |
| 14 | 10 | 15 | 11 | 14 | 10 | 15 | 11 | 14 | 10 | 15 | 11 |
| 0 | 4 | 1 | 5 | 0 | 4 | 1 | 5 | 0 | 4 | 1 | 5 |
| 12 | 8 | 13 | 9 | 12 | 8 | 13 | 9 | 12 | 8 | 13 | 9 |
| 2 | 6 | 3 | 7 | 2 | 6 | 3 | 7 | 2 | 6 | 3 | 7 |
| 14 | 10 | 15 | 11 | 14 | 10 | 15 | 11 | 14 | 10 | 15 | 11 |

FIG. 9

RETINAL PROSTHESIS WITH EFFICIENT PROCESSING CIRCUITS

CROSS-REFERENCE TO RELATED APPLICATION

The present application is a continuation of U.S. patent application Ser. No. 13/034,516, entitled "RETINAL PROSTHESIS WITH EFFICIENT PROCESSING CIRCUITS," filed Feb. 24, 2011, which published as US 2012/0221103 to Liran et al., on Aug. 30, 2012, which is incorporated herein by reference.

This application is related to U.S. patent application Ser. No. 12/852,218, entitled "Retinal Prosthesis Techniques," filed Aug. 6, 2010, which published as US 2012/0035725 and issued as U.S. Pat. No. 8,428,740 and which is incorporated herein by reference.

FIELD OF THE INVENTION

The present invention relates generally to medical devices, and specifically to retinal prostheses for restoring or enhancing visual function.

BACKGROUND OF THE INVENTION

Retinal malfunction is a leading cause of blindness and visual impairment. Implantation of a retinal prosthesis in the eye may be effective in restoring some useful vision in individuals suffering from blindness of retinal origin. A variety of retinal prostheses have been described in the patent literature.

SUMMARY

Embodiments of the present invention that are described herein below provide retinal prostheses and circuits and methods for enhancing performance and reducing power consumption of such prostheses.

There is therefore provided, in accordance with an embodiment of the present invention, a medical device, including an array of electrodes, configured for implantation in contact with tissue in an eye of a living subject. Driver circuitry is configured to drive the electrodes in an alternating pattern, such that different groups of the electrodes are driven to stimulate the tissue during different, predetermined respective time periods.

In some embodiments, the driver circuitry is configured to hold the electrodes at a common potential in time intervals outside the respective time periods so that the electrodes serve as return electrodes during the time intervals. The driver circuitry may include memory elements for returning the electrodes to a common level following the respective time periods.

In a disclosed embodiment, some of the different time periods overlap, and the groups are selected so that the time periods during which mutually-adjacent electrodes are driven do not overlap.

There is also provided, in accordance with an embodiment of the present invention, a medical device, including a first array of electrodes, configured for implantation in contact with tissue in an eye of a living subject. Light-sensing elements in a second array are configured to output respective signals in response to light that is incident on the elements. Conversion circuits in a third array are coupled to receive from the second array the signals from the light-sensing elements and a representation of a mean level of the signals, and to generate pulses to drive the electrodes at respective frequencies determined responsively to differences between the signals and the representation of the mean level.

In disclosed embodiments, the device includes a common voltage reconstruction circuit, which is configured to receive inputs corresponding to the respective signals output by the light-sensing elements and to output the representation of the mean level to the conversion circuits.

The representation of the mean level may include a function of a mean value of the signals, such as a multiple of the mean value or a time-filtered mean value.

There is additionally provided, in accordance with an embodiment of the present invention, a medical device, including a first array of electrodes, configured for implantation in contact with tissue in an eye of a living subject. Light-sensing elements in a second array are configured to output respective signals in response to light that is incident on the elements. Conversion circuits in a third arrays are coupled to receive the signals from the light-sensing elements, and to generate pulses to drive the electrodes at respective frequencies determined responsively to the signals, including an overshoot in the frequencies in response to a change in an intensity of the incident light on a given light-sensing element.

Typically, the overshoot includes a transient increase in a frequency applied to a given electrode in response to an increase in the intensity incident on the given light-sensing element and may include a transient decrease in the frequency applied to the given electrode in response to a decrease in the intensity.

In a disclosed embodiment, the conversion circuits include a low-pass filter for generating the overshoot, wherein the low-pass filter includes a series of capacitive elements that are switched in sequence to generate a low-pass response.

There is further provided, in accordance with an embodiment of the present invention, a medical device, including a first array of electrodes, configured for implantation in contact with tissue in an eye of a living subject, and a second array of driver circuits. Each driver circuit is configured to drive a respective electrode in the first array with pulses responsively to an intensity of light that is incident on a respective area of the eye and includes a memory element for returning the respective electrode to a common level following each pulse.

In a disclosed embodiment, the memory element includes a flip-flop, and the driver circuits are operative to provide balanced stimulation to the tissue. The driver circuits may contain a discharge path for protecting the device from electrostatic discharge.

There is moreover provided, in accordance with an embodiment of the present invention, a medical device, including a first array of electrodes, configured for implantation in contact with tissue in an eye of a living subject, and a second array of driver circuits. Each driver circuit is configured to drive a respective electrode in the first array responsively to an intensity of light that is incident on a respective area of the eye. A power source is coupled to supply electrical power to the driver circuits, and a power sensor is coupled to deactivate a first group of the electrodes when the electrical power drops below a predetermined threshold, while a second group of the electrodes remains active.

In one embodiment, the second group includes the electrodes within a selected region of the first array, while the first group includes the electrodes outside the region. In an alternative embodiment, the first and second groups of the electrodes are interleaved in the first array.

Typically, the power sensor is configured to monitor a voltage output by the power supply and to deactivate the first group of the electrodes when the voltage drops below the predetermined threshold. The power sensor may be configured to compare the voltage output to a plurality of thresholds and reduce a number of active electrodes further as each threshold is passed.

In one embodiment, the power sensor is configured to be implanted in the eye together with the arrays of electrodes and driver circuits. In an alternative embodiment, the power sensor is configured to be located outside the eye and to transmit signals into the eye in order to activate and deactivate the electrodes.

There is furthermore provided, in accordance with an embodiment of the present invention, a method for neural stimulation, which includes providing an array of electrodes for implantation in contact with tissue in an eye of a living subject. The electrodes are driven in an alternating pattern, such that different groups of the electrodes are driven to stimulate the tissue during different, predetermined respective time periods.

There is also provided, in accordance with an embodiment of the present invention, a method for neural stimulation, which includes providing a first array of electrodes for implantation in contact with tissue in an eye of a living subject. A second array of light-sensing elements outputs respective signals in response to light that is incident on the elements. Pulses are generated to drive the electrodes at respective frequencies determined responsively to differences between the signals output by the light-sensing elements and a representation of a mean level of the signals.

There is additionally provided, in accordance with an embodiment of the present invention, a method for neural stimulation, which includes providing a first array of electrodes for implantation in contact with tissue in an eye of a living subject. A second array of light-sensing elements outputs respective signals in response to light that is incident on the elements. Pulses are generated to drive the electrodes at respective frequencies determined responsively to the signals, including an overshoot in the frequencies in response to a change in an intensity of the incident light on a given light-sensing element.

There is further provided, in accordance with an embodiment of the present invention, a method for neural stimulation, which includes providing an array of electrodes for implantation in contact with tissue in an eye of a living subject. The electrodes in the array are driven with pulses responsively to an intensity of light that is incident on a respective area of the eye. Memory elements are coupled to return the electrodes to a common level following each pulse.

There is moreover provided, in accordance with an embodiment of the present invention, a method for neural stimulation, which includes providing an array of electrodes for implantation in contact with tissue in an eye of a living subject. The electrodes in the array are driven responsively to an intensity of light that is incident on an area of the eye. A first group of the electrodes is deactivated when a level of electrical power supplied for driving the electrodes drops below a predetermined threshold, while continuing to drive a second group of the electrodes.

The present invention will be more fully understood from the following detailed description of the embodiments thereof, taken together with the drawings in which:

BRIEF DESCRIPTION OF THE DRAWINGS

FIG. 9 is a block diagram that schematically illustrates an order of stimulation of an array of electrodes, in accordance with an embodiment of the present invention;

DETAILED DESCRIPTION OF EMBODIMENTS

Overview

Figure 1:
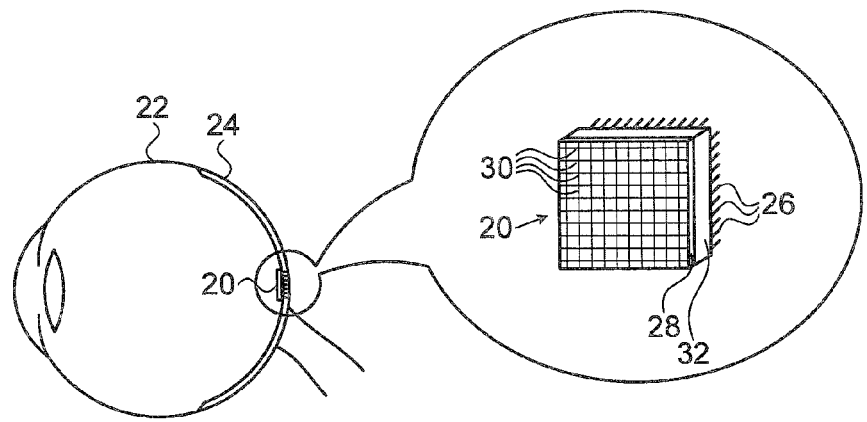
FIG. 1 is a schematic, pictorial illustration of a retinal prosthesis implanted in an eye, in accordance with an embodiment of the present invention.

Although many retinal prostheses have been proposed in the scientific and patent literature, substantial technical challenges remain in practical implementations of such devices. On the one hand, to mimic natural visual function, such devices should be able to sense light and provide effective neural stimulation with high resolution and high dynamic range. At the same time, because of space limitations and physiological constraints, the circuits of the prosthesis can consume only minimal electrical power. Generally speaking, there is a tradeoff between the efficiency of the electrical circuits and the sensitivity and resolution that the prosthesis can attain.

Embodiments of the present invention that are described hereinbelow address these issues by providing novel, highly efficient processing circuitry for a retinal prosthesis. This circuitry may be integrated with light sensors, electrodes, and other components of retinal prostheses that are described in PCT International Publication WO 2010/089739 and in the above-mentioned U.S. patent application Ser. No. 12/852, 218 which published as US 2012/0035725 and issued as U.S. Pat. No. 8,428,740, whose disclosures are incorporated herein by reference.

In the disclosed embodiments, a retinal prosthesis device comprises an array of electrodes, which are implanted so as to contact tissue in the eye of a subject. In some of these embodiments, driver circuits drive the electrodes in an alternating pattern, in which different groups of the electrodes are driven to stimulate the tissue during different, predetermined respective time periods. The groups of the electrodes may be selected geometrically within the array so that the time periods during which mutually-adjacent electrodes are driven do not overlap. Typically, the driver circuits hold the electrodes at a common potential (high or low, depending on the polarity of stimulation) outside their assigned time periods so that the electrodes serve as return electrodes when not applying stimulation.

As a result of these measures, nearly all the energy applied by the driver circuits goes to actually stimulate the neurons in the eye, and wasted energy is minimized. Furthermore, by stimulating different groups of electrodes at different times, an approximately uniform level of overall power output by the circuits can be maintained, thus avoiding large variations in power consumption over time and enhancing efficiency.

In some embodiments, light-sensing elements in the retinal prosthesis output respective signals to conversion circuits, which also receive as input a mean level of the signals from the light-sensing elements. Each conversion circuit generates pulses to drive an electrode at a frequency that depends on the differences between the signal level output by a respective light sensing element (or group of elements) and the mean level. The "mean" that is used by the conversion circuits may be local or global and may comprise any suitable sort of combination of the signal levels, such as a linear, logarithmic, or weighted average or a more complex function. The use of this sort of mean reference level in generating the output pulses to the electrodes enables the prosthesis to compress the large input dynamic range of the light-sensing elements into a much smaller output dynamic range to the electrodes without significant loss of visual information, in a manner similar to the natural functioning of the human eye.

The conversion circuits may be configured to generate an overshoot in the respective frequencies in response to a changes in an intensity of the incident light on a given light-sensing element. This overshoot typically comprises a transient increase in a frequency in response to an increase in light intensity and may also cause a transient decrease in the frequency in response to a decrease in the intensity, mimicking the response of biological light sensing cells in the retina.

It may sometimes occur that the electrical power available to the retinal prosthesis drops below the minimum level needed to run all the circuits of the prosthesis. To deal with this eventuality, while still maintaining some visual function, an embodiment of the present invention provides a power sensor, which deactivates a certain group of the channels in the prosthesis when the electrical power drops below a given threshold, while keeping the remaining electrodes active. The active group may comprise the electrodes within a selected region of the array—meaning that the field of view contracts. Alternatively, the active electrodes may be interleaved with the deactivated electrodes, resulting in reduced resolution.

In the figures and in the explanation that follows, a retinal prosthesis having all of the above features is described. In alternative embodiments, however, only one or a few of the above features may be implemented, possibly in conjunction with other circuits and techniques that are known in the art. All of these embodiments are considered to be within the scope of the present invention.

System Description

FIG. 1 is a schematic, pictorial illustration of a retinal prosthesis 20 implanted in an eye 22, in accordance with an embodiment of the present invention. In the pictured embodiment, prosthesis 20 is implanted epiretinally, and the rear side of prosthesis 20 comprises an array of electrodes 26, which protrude into or otherwise contact retinal tissue 24, as described, for example, in the above-mentioned WO 2010/089739 and U.S. Ser. No. 12/852,218 which published as US 2012/0035725 and issued as U.S. Pat. No. 8,428,740. Alternatively, the prosthesis may be implanted subretinally. The front side of the prosthesis comprises an array 28 of light-sensing elements 30, such as photodiodes (PD), which output signals in response to light that is focused onto them by the eye.

Conversion circuitry 32 receives and processes the output signals from elements 30 in order to generate pulses to drive electrodes 26. Typically, the frequencies of these pulses depend on the intensity of the light incident on elements 30, as explained in greater detail hereinbelow. In the description that follows, it is assumed that there is a one-to-one correspondence between light-sensing elements 30 and electrodes 26, i.e., circuitry 32 drives each electrode in response to a corresponding light-sensing element. Alternatively, other relations between light-sensing elements and electrodes are possible, such as each electrode being driven in response to a number of neighboring light-sensing elements. Furthermore, although the arrays of light-sensing elements and electrodes in FIG. 1 are shown as rectilinear, other geometrical arrangements are possible, including both uniformly-spaced and non-uniformly-spaced arrays.

Typically, circuitry 32 comprises one or more semiconductor chips, in which the analog and digital circuit elements described below are fabricated, using methods of integrated circuit production that are known in the art. Array 28 of light-sensing elements 30 may be integrated into the same chip (or chips) as circuitry 32. Alternatively, array 28 may be fabricated on a separate substrate, and elements 30 may be coupled to the processing channels of circuitry 32 using methods that are known in the art. Electrodes 26 may be fixed to the rear side of prosthesis 20 using through-silicon vias (TSV), for example, or other methods described in the above-mentioned WO 2010/089739 and U.S. Ser. No. 12/852,218 which published as US 2012/0035725 and issued as U.S. Pat. No. 8,428,740.

Figure 2:
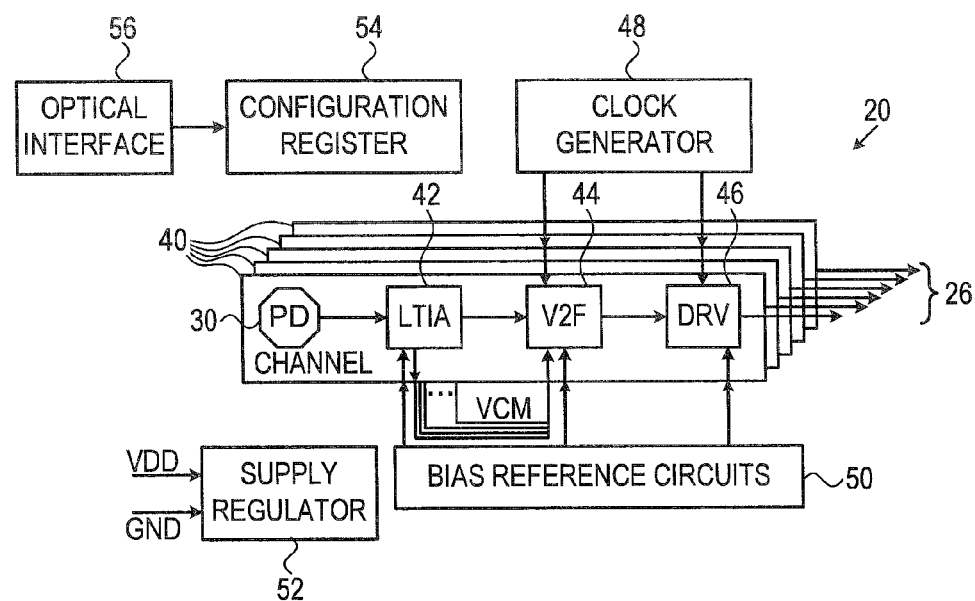
FIG. 2 is a block diagram that schematically illustrates electronic circuitry in a retinal prosthesis, in accordance with an embodiment of the present invention.

FIG. 2 is a block diagram that schematically illustrates electronic circuitry in prosthesis 20, in accordance with an embodiment of the present invention. Prosthesis 20 comprises multiple parallel channels 40 each comprising a respective light sensing element 30 (represented as a photodiode—PD) and associated conversion circuitry. Elements 30 and the corresponding channels 40 are arranged in a two-dimensional array, as illustrated in FIG. 1. To provide good visual resolution, prosthesis 20 may comprise approximately 1000 such channels, but larger or smaller numbers of channels may alternatively be provided, depending on application requirements and technological capabilities and constraints.

In the disclosed embodiments, the conversion circuitry in each channel 40 comprises the following circuit components:
  A logarithmic trans-impedance amplifier (LTIA) 42, which converts the photocurrent output by the corresponding photodiode to a voltage, with a logarithmic transfer function. Amplifiers of this sort are known in the art, as described, for example, by Delbruck and Mead in "Analog VLSI Adaptive, Logarithmic, Wide-Dynamic-Range Photoreceptor," 1994 International Symposium on Circuits and Systems (London, 1994), pages 339-342, which is incorporated herein by reference.
  A voltage-to-frequency (V2F) converter 44 converts the log of the light intensity that is output by LTIA 42 to a stimulation frequency. To mimic the human eye and compress the dynamic range of the signals, the frequency output of V2F converter 44 depends not only on the local intensity sensed by the corresponding light-sensing element 30, but also on the difference between the output of LTIA 42 relative to that in other channels 40. For this purpose, each V2F converter 44 receives a common voltage (VCM) input, representing a mean over the channels in the array. In one embodiment, this mean is simply an arithmetic average over all the channels; but the mean may alternatively be locally-weighted or otherwise adjusted. Details of the V2F converter are described below with reference to the figures that follow.

A driver (DRV) circuit 46 generates a train of pulses to drive the corresponding electrode 26 at the frequency provided by V2F converter 44. Details of the driver circuit are described below with reference to FIGS. 7 and 8.

A clock generator 48 synchronizes the operation of V2F converters 44 and drive circuits 46. The clock generator outputs multiple different clock phases, for example, sixteen different phases, which are distributed to different groups of channels 40. As a result, different groups of channels are activated at different times to drive the corresponding electrodes 26. The remaining electrodes may serve as ground returns during the inactive periods of the corresponding channels. Alternatively, prosthesis 20 may comprise one common electrode, or a local return per channel or group of channels. This staggered pattern of channel timing is described in greater detail below with reference to FIGS. 9 and 10.

Bias reference circuits 50 provide reference voltages for biasing the current sources in all the analog circuits of channels 40. Circuits 50 receive power from a supply regulator 52, which also provides power to the other components of prosthesis 20. The power may be supplied by transduction of optical energy that is projected into the eye, as described in the above-mentioned WO 2010/089739 and U.S. Ser. No. 12/852,218 which published as US 2012/0035725 and issued as U.S. Pat. No. 8,428,740, or from any other suitable power source. When the available power drops below a certain level, the power supply and switching circuits 50 may shut off power to certain channels 40, while using the limited available power to maintain functionality within a limited group of the channels. This power adaptation functionality is described below with reference to FIG. 11.

Various parameters of prosthesis 20 may be modified in order to adapt to the physiology of the patient in whose eye the device is implanted and to adjust for changes that may occur over time. For example, an operator may adjust the level of the pulses output by driver circuits 46 so that they are just sufficient to engender neural stimulation and no higher, thereby reducing wasted energy. The values of the various adjustable parameters are held in a configuration register 54. An optical interface 56 is driven by a coded light beam, which is projected into the eye, and sets the values in register 54 in accordance with the encoded data carried by the beam.

Voltage-to-Frequency Conversion

Figure 3:
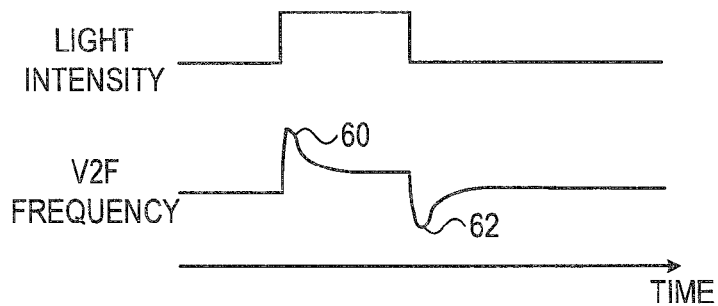
FIG. 3 is a plot that schematically illustrates the response of a retinal prosthesis to incident light, in accordance with an embodiment of the present invention.

FIG. 3 is a plot that schematically illustrates the response of V2F converter 44 to incident light, in accordance with an embodiment of the present invention. The upper trace in the plot shows the incident light intensity on a given light-sensing element 30, including a transient increase in the intensity, followed by a return to the previous intensity level. The lower trace shows the frequency output of the corresponding V2F converter 44. As in the human eye, changes in the light intensity lead to overshoots 60 and 62 in the V2F frequency: At overshoot 60, the frequency increases in response to the intensity increase before decaying to a stable level, whereas at overshoot 62 (sometimes referred to as an undershoot), the frequency drops briefly below the baseline level in response to the intensity decrease. To mimic human visual function, overshoots 60 and 62 decay with time constants on the order of tens to a few hundred milliseconds.

Figure 4A:
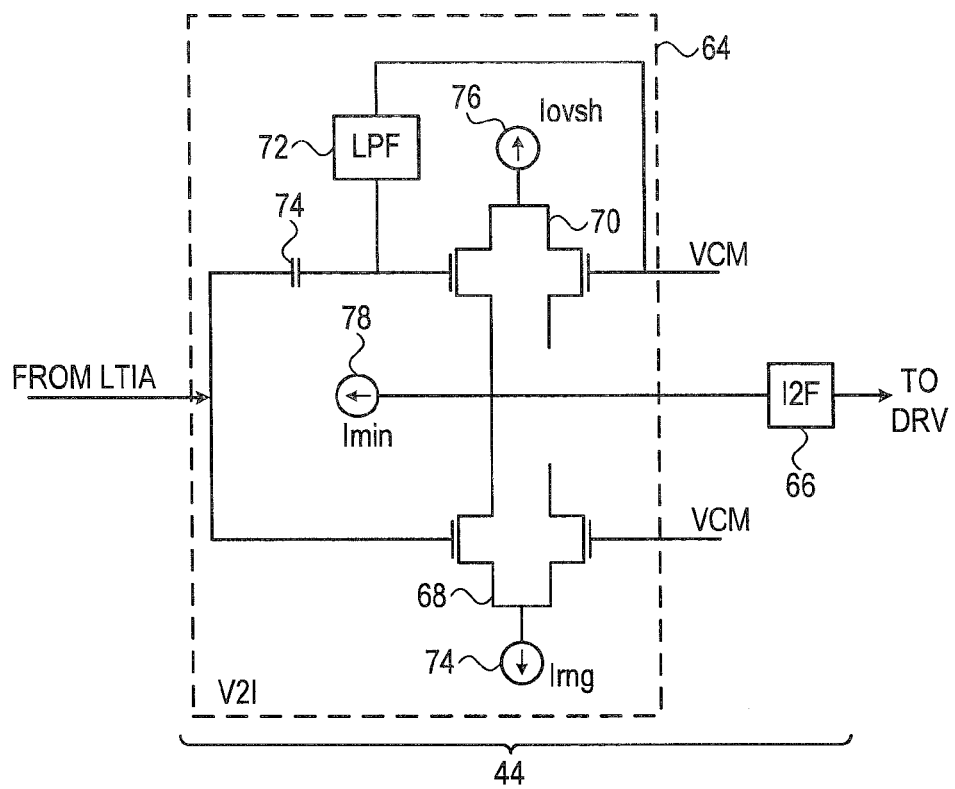
FIG. 4A is an electrical schematic diagram of a voltage-to-frequency converter, in accordance with an embodiment of the present invention.

FIG. 4A is an electrical schematic diagram of V2F converter 44, in accordance with an embodiment of the present invention. This converter implements the overshoot response shown in FIG. 3, within a very compact, low-power design. Converter 44 comprises two sub-circuits: a voltage-to-current (V2I) converter 64 followed by a current-to-frequency (I2F) converter 66. Together these elements typically consume about 0.1 µW of electrical power, or less.

V2I converter 64 comprises a main differential amplifier 68 and/or an overshoot amplifier 70, driven by respective current sources 74 (Irng) and 76 (Iovsh). A baseline current source 78 (Imin) generates a minimum current output level to I2F converter 66. Main amplifier 68 receives as inputs the voltage output from the corresponding LTIA 42 and a representation of the mean voltage level VCM, as noted above. This representation may be the mean value itself, or it may comprise some function of the mean, such as a multiple of the mean (by a coefficient greater than or less than one) or a time-filtered mean value. Overshoot amplifier 70 has a high-pass response due to a series capacitor 74 and a parallel low-pass filter (LPF) 72. This low-pass filter is used here due to the difficulty of implementing high-pass filters with low cut-off frequencies (requiring large capacitance and resistance values) in an integrated circuit.

I2F converter 66 outputs a train of pulses to drive circuit 46, at a frequency that is proportional to the current output of V2I converter 64. The minimum frequency output, in dark conditions, is typically below 10 Hz, while the maximum frequency, during periods of overshoot, may exceed 200 Hz. The pulses output by the I2F converter typically have constant amplitude, usable by the logic circuits in driver circuit 46. The pulses from the I2F converter stimulate driver circuit 46 to generate output pulses to the electrodes with proper timing, as described below. The pulses output from I2F converter 66 may be gated by clock generator 48 (FIG. 2), so that each driver circuit 46 is pulsed only during its assigned active periods. Alternatively, the pulses output from the I2F circuit may be ungated. The pulses from the I2F converter may be timed, and the driver circuits suitably designed, to provide balanced stimulation of the tissue: All charge applied to stimulate the tissue in a given pulse is discharged by the next pulse, as described further hereinbelow.

Figure 4B:
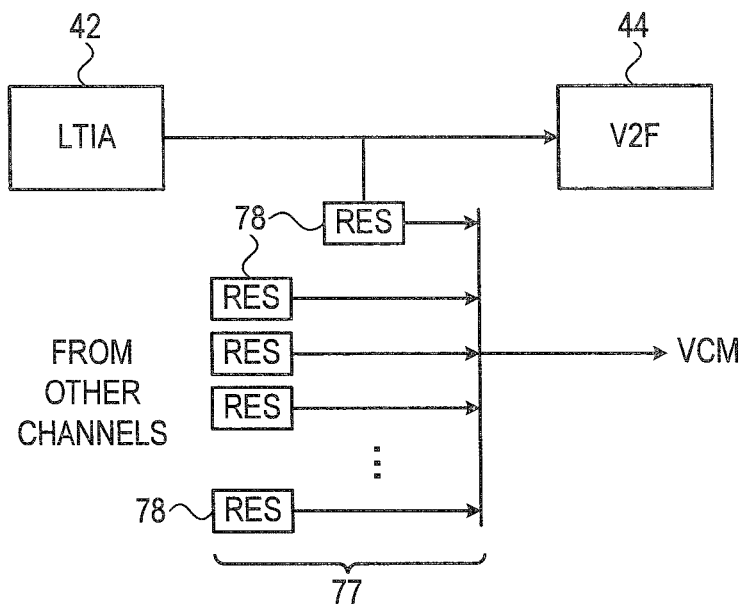
FIGS. 4B-4D are electrical schematic diagrams of common voltage reconstruction circuits, in accordance with embodiments of the present invention.
Figure 4C:
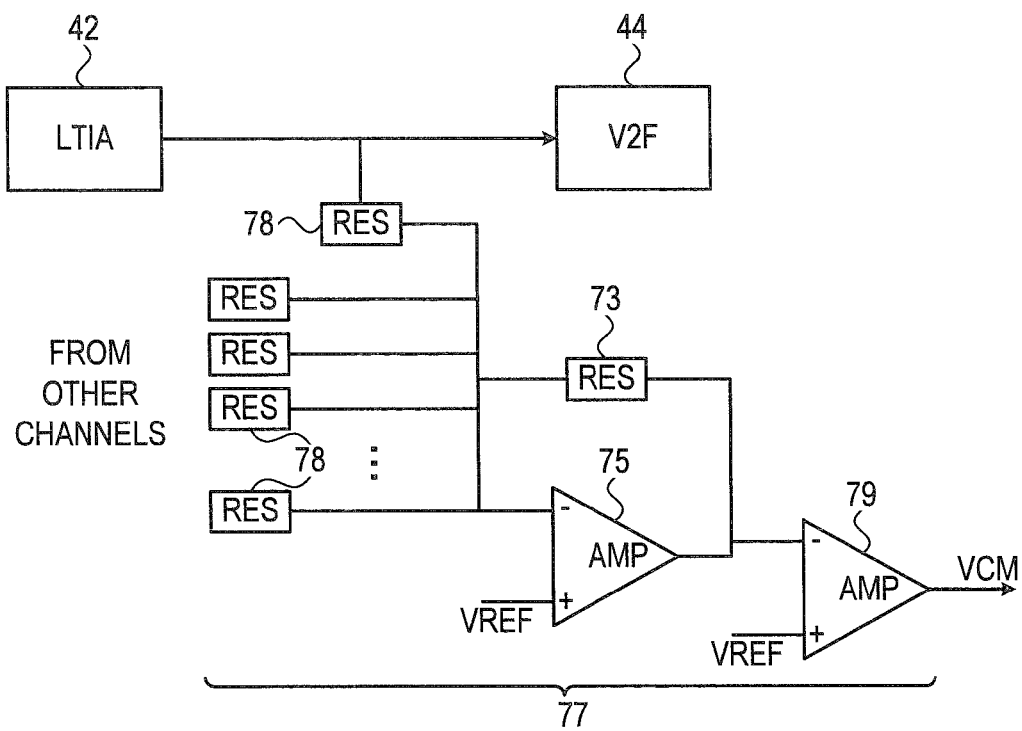
Figure 4D:
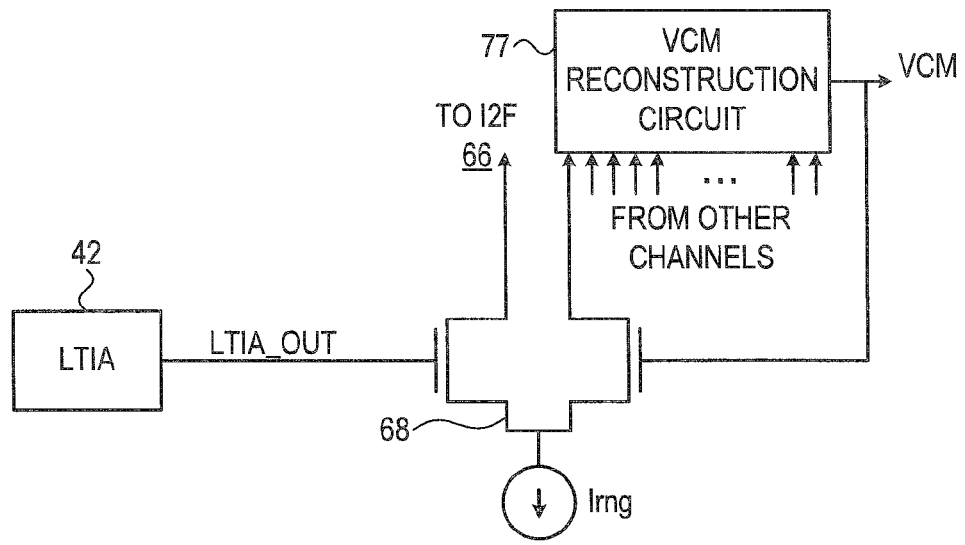

FIGS. 4B-4D are electrical schematic diagrams of common voltage reconstruction circuits 77, in accordance with a number of embodiments of the present invention. These circuits generate the VCM input to V2F converter 44. In the embodiment shown in FIG. 4B, the outputs from LTIAs 42 in all the channels 40 of prosthesis 20 (or of a selected set of the channels) are coupled together via parallel resistors 78 to generate VCM as a sum of the outputs. Resistors 78 typically have substantially higher resistance than the input resistance of V2F converter 44. Alternatively, as shown in FIG. 4C, the resistors may be coupled together to the input of a differential amplifier 75 with a feedback resistance 73. The output of amplifier 75 drives a second differential amplifier 79 to generate VCM.

FIG. 4D schematically illustrates yet another arrangement in which a feedback loop is generated by the unused output of main amplifier 68 in V2I converter 64 and thus provides a current output to VCM reconstruction circuit 77. This current is in inverse linear proportion to the output of LTIA 42. Circuit 77 combines these currents over all the channels to generate VCM.

Figure 5A:
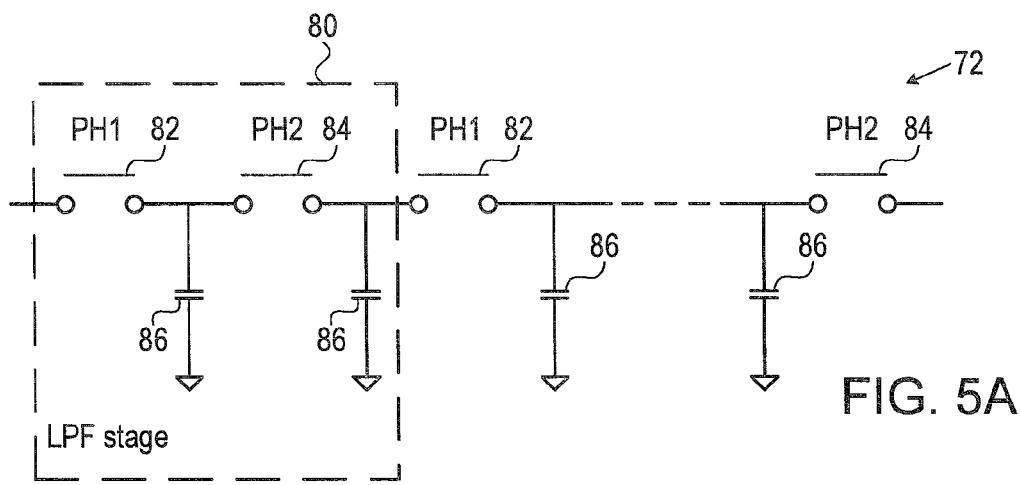
FIG. 5A is an electrical schematic diagram of a switched low-pass filter, in accordance with an embodiment of the present invention.
Figure 5B:
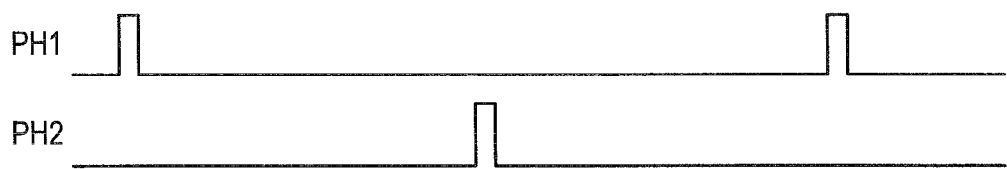
FIG. 5B is a timing diagram showing switching signals applied to the low-pass filter of FIG. 5A.
Figure 6A:
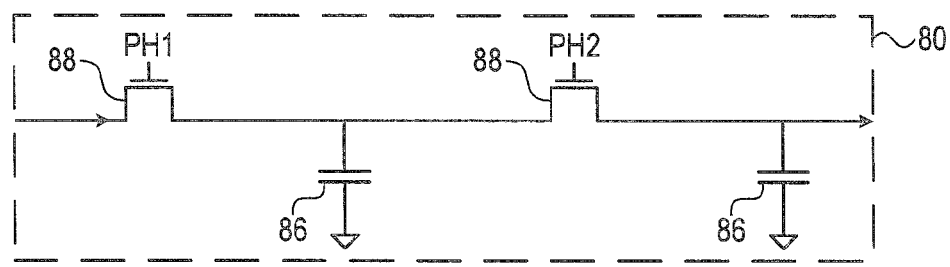
FIGS. 6A-6D are electrical schematic diagrams of switched low-pass filters, in accordance with alternative embodiments of the present invention.
Figure 6B:
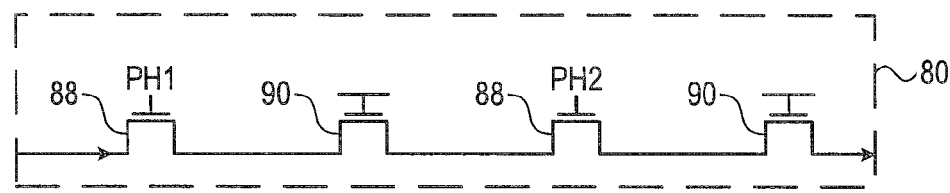
Figure 6C:
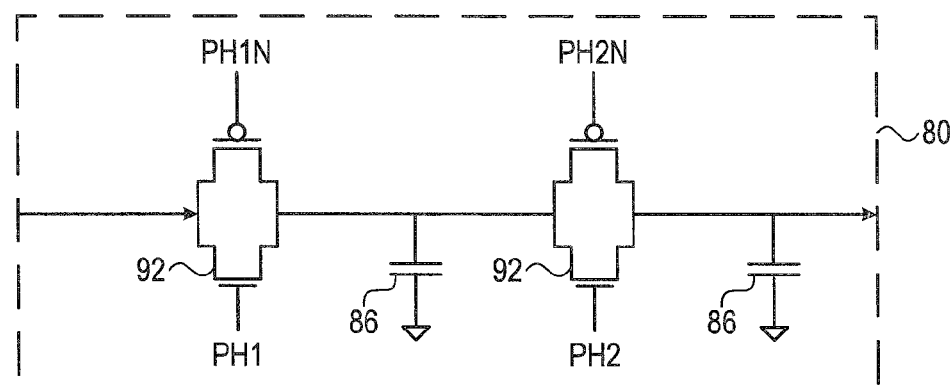
Figure 6D:
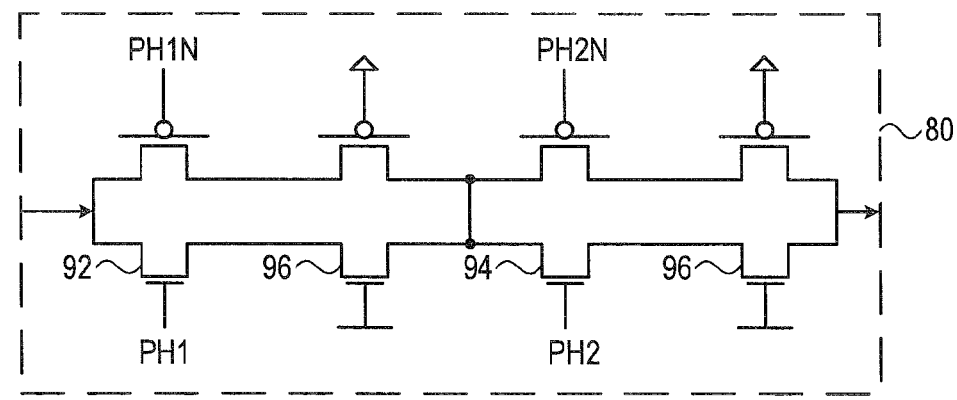

FIGS. 5A and 5B schematically illustrate the design and operation of low-pass filter 72, in accordance with an embodiment of the present invention. FIG. 5A is an electrical schematic diagram, while FIG. 5B is a timing diagram showing switching signals applied to the low-pass filter. Filter 72 uses a switched-capacitor design to circumvent the need for a high-value resistor in the low-pass filter. This filter can be implemented either by a single stage or by multiple cascaded stages, as shown in FIG. 5A. The use of multiple stages has the advantage of higher sampling frequency, and thus enables higher input bandwidth relative to designs with fewer stages at lower sampling frequency.

Filter 72 comprises a chain of multiple stages 80, each comprising two shunt capacitors 86, which are connected in series by two switches 82 and 84. The switches are closed in alternation by clock signals PH1 and PH2. The alternating operation of switches 82 and 84 provides the low-pass response, with a time constant controlled by the number of stages 80 and the frequency of the clock signals. The switches can be implemented using very small transistors. Coupling the capacitors to ground, as shown in FIG. 5A, reduces sensitivity to supply noise. Thus, filter 72 is well-suited to providing the required long time constant within an integrated circuit under the severe size and power constraints of prosthesis 20. The capacitors can be implemented by any structure with sufficient capacitance, such as metal-to-metal capacitors, poly-to-poly capacitors, gates of MOS transistors, or reverse-biased PN diodes.

FIGS. 6A-6D are electrical schematic diagram of one stage 80 in a switched low-pass filter, in accordance with alternative embodiments of the present invention. The stages shown in FIGS. 6A-6D may be used, for example, in place of each stage 80 in filter 72 (FIG. 5A). Thus, the function of switches 82 and 84 may be implemented by single-transistor switches 88 or by dual switches 92 and 94, each comprising a pair of transistors that are driven by clock signals of positive polarity (PH1, PH2) and negative polarity (PH1N, PH2N), respectively. The function of capacitors 86 is performed in FIG. 6B by transistors 90, or by pairs of transistors 96 in FIG. 6D, in which one transistor is tied to VDD and the other to ground, thus providing the required shunt capacitance.

Various alternative implementations of this sort of switched-capacitor chain will be apparent to those skilled in the art and are considered to be within the scope of the present invention.

Driver Circuits

Figure 7:
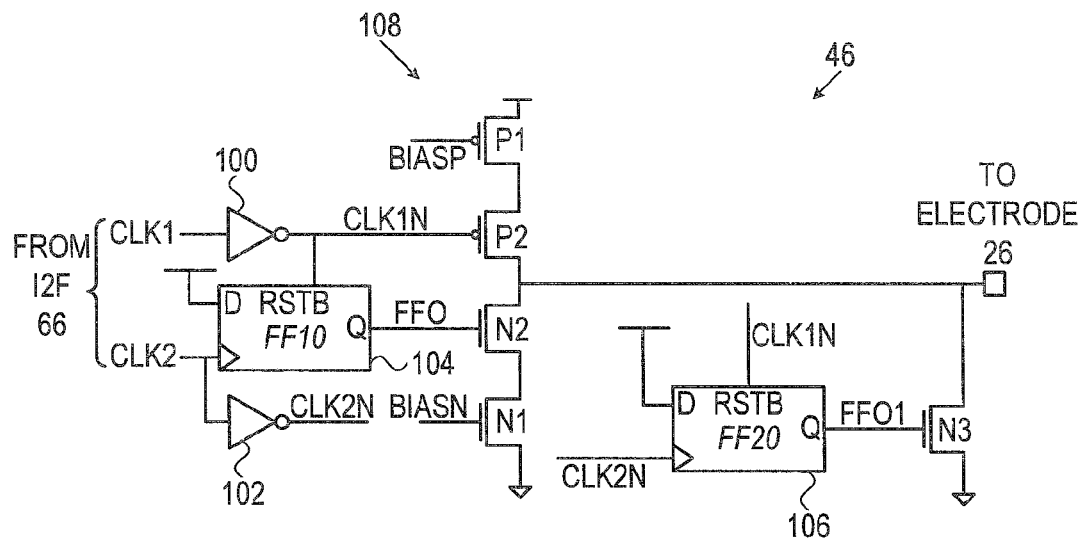
FIG. 7 is an electrical schematic diagram of a driver circuit, in accordance with an embodiment of the present invention.
Figure 8:
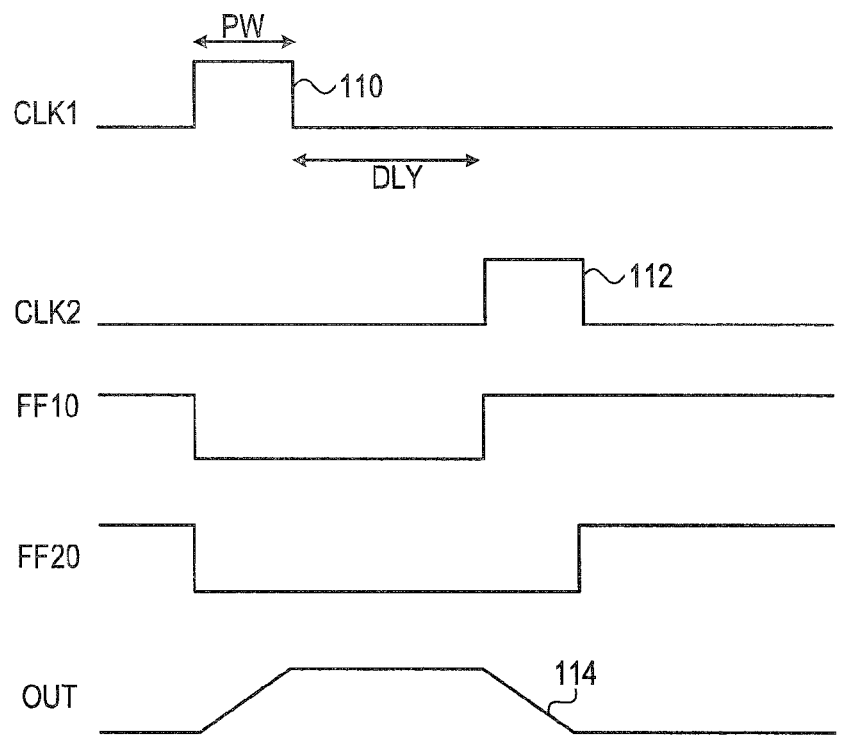
FIG. 8 is a timing diagram showing signals generated in the driver circuit of FIG. 7.

Reference is now made to FIGS. 7 and 8, which schematically illustrate the design and operation of driver circuit 46, in accordance with an embodiment of the present invention. FIG. 7 is a schematic circuit diagram of driver circuit 46, while FIG. 8 is a timing diagram showing signals received and generated by the circuit. FIGS. 7 and 8 illustrate a driver circuit that outputs pulses of positive polarity to electrode 26, but this design may readily be modified to generate pulses of negative polarity, as will be evident to those skilled in the art.

In the pictured embodiment, I2F converter 66 outputs pairs of clock pulses 110 and 112, labeled CLK1 and CLK2, which have a fixed pulse width (PW) and are separated by a fixed delay (DLY). Typically, the pulse widths and the delay are in the range of 50-500 µs. The pulse widths and delay determine the duration and rise and fall times of output pulses 114 from driver circuit 46 to electrode 26, and thus control the amount of charge that is delivered to the tissue in each pulse. These pulse parameters may be adjusted to match the activation threshold of the neurons that are stimulated by the electrodes.

The repetition frequencies of clock pulses 110 and 112 determine the frequency of the pulses output by the driver circuit, and hence the intensity of stimulation that is applied to the tissue by the corresponding electrode.

The input clock pulses CLK1 and CLK2 are inverted by inverters 100 and 102 to generate the inverse clock signals CLK1N and CLK2N, and these four clock signals together drive flip-flops 104, 106 and switching logic 108. The switching logic comprises bias transistors P1 and N1, which are driven by bias currents BIASP and BIASN from bias reference circuit 50 (FIG. 2). The remaining transistors P2, N2 and N3 are driven by the input clock pulses and by the outputs of the flip-flops, FF10 and FF20, as shown in FIG. 8.

In operation of driver circuit 46, flip-flops 104 and 106 serve as memory elements to pull electrode 26 back to the common level (ground) after the pulse. The rising edge of the CLK1 signal resets flip-flops 104 and 106, disconnecting the pull-down path of the driver circuit and activating the pull-up path through transistors P1 and P2. As a result, the VDD voltage charges the output to electrode 26 during pulse 110. The rising edge of CLK2 then sets flip-flop 104, thus activating the pull-down path through transistors N1 and N2. At the falling edge of CLK2, flip-flop 106 is set, and adds N3 to the pull-down path.

As a result of the pull-down by flip-flops 104 and 106, the voltage on electrode 26 is tied to ground with low resistance in between stimulation pulses. The resistance of transistor N3 is typically less than 500 ohms. Consequently, during periods in which a given driver circuit 46 is not actively outputting pulses, the corresponding electrode 26 serves well as a return electrode for the active electrodes in its neighborhood. This dual functionality of electrodes 26—as stimulating electrodes and return electrodes at different times—obviates the need for dedicated return electrodes and works efficiently in conjunction with the interleaved stimulation times of different groups of electrodes, as described in detail in the next section. The design of driver circuit 46 and the timing of the pulses applied to control the driver circuit ensure that the tissue receives balanced stimulation from the electrodes.

Referring now to the details of switching logic 108, transistor P1 acts as a pull-up current source, with BIASP generated by a current mirror transistor, which could be common to many driver circuits or the whole array. Similarly, transistor N1 acts as a pull-down current source, with BIASN generated by a current mirror transistor like BIASP. The amount of charging is held equal to the amount of discharging by matching the pull up current of P1 with the pull-down current of N1 and by matching the pulse widths of CLK1 and CLK2. In case there is residual charge at the end of the pulse, it will be discharged by transistors N1, N2 and N3, which are conducting after the end of the pulse.

The use of switched current sources in circuit 46 (as opposed to voltage switching) enables the output voltage level to be controlled simply by controlling the charging current and charging time. This design eliminates momentarily high currents, which could drop the supply voltage and might damage the tissue contacted by the electrodes due to high current density.

The output circuit to electrode 26 may be exposed to contact with the human body during production of the device and during surgical implantation. For this reason, it is desirable that the electrodes be immune to electrostatic discharge (ESD) stress. Transistor N3 may therefore be configured to provide a discharge path to ground, in order to increase the immunity of prosthesis 20 to ESD.

As noted earlier, the circuit design and waveforms that are shown in FIGS. 7 and 8 may be modified in a straightforward manner to generate pulses of negative polarity, instead of the positive-polarity configuration that is shown in the figures. In such a negative-polarity configuration, the pull-down functions and circuit components described above for returning the electrodes to the common ground level are replaced by pull-up to a common high level, such as the VDD level.

These common ground and high levels are referred to herein collectively simply as common levels. Although the embodiment shown in these figures uses flip-flops to carry out this return-to-common function, other suitable types of memory elements may similarly be used for this purpose.

Interleaving of Stimulation Times

FIG. 9 is a block diagram that schematically illustrates an alternating pattern of stimulation of the array of electrodes in prosthesis 20, in accordance with an embodiment of the present invention. In this figure, the squares represent driver circuits 46 in different channels 40 of the prosthesis. The channels and the corresponding electrodes are arranged in a rectilinear array, which is arranged as shown in the figure. Although for the sake of simplicity, FIG. 9 represents only a 12×12 array, the same sort of pattern may be applied over larger electrode arrays.

Each channel 40 (including the corresponding driver circuit 46) is assigned to one of sixteen groups, which are numbered in serial order from 0 to 15. Thus, the array is divided up into blocks 122 of 4×4 channels, as shown in the figure, with one channel in each block belonging to each of the groups. (Alternatively, a larger or smaller number of groups may be assigned.) The group numbers indicate the order in which driver circuits 46 are activated. During the active period of its driver circuit, each electrode 26 stimulates the tissue with which it is in contact, following which the driver circuit ties the electrode to ground so that the electrode serves as a return electrode for its neighbors, as explained above. Thus, while the driver circuits in group 12, for example, are active in stimulating the tissue, the neighboring driver circuits in groups 0, 1, 2, 3, 4, 6, 8 and 9 serve as return paths.

Splitting the activation time of the electrodes among multiple phases is useful in avoiding overload of the power supply in prosthesis 20, which may have high serial resistance. When using multiple phases as shown in FIG. 9, for example, only a fraction of the driver circuits will be active simultaneously at any given time, thus spreading the current load evenly across the entire stimulation period uniformly in the most extreme case. This method minimizes possible voltage drop from the supply.

Figure 10:
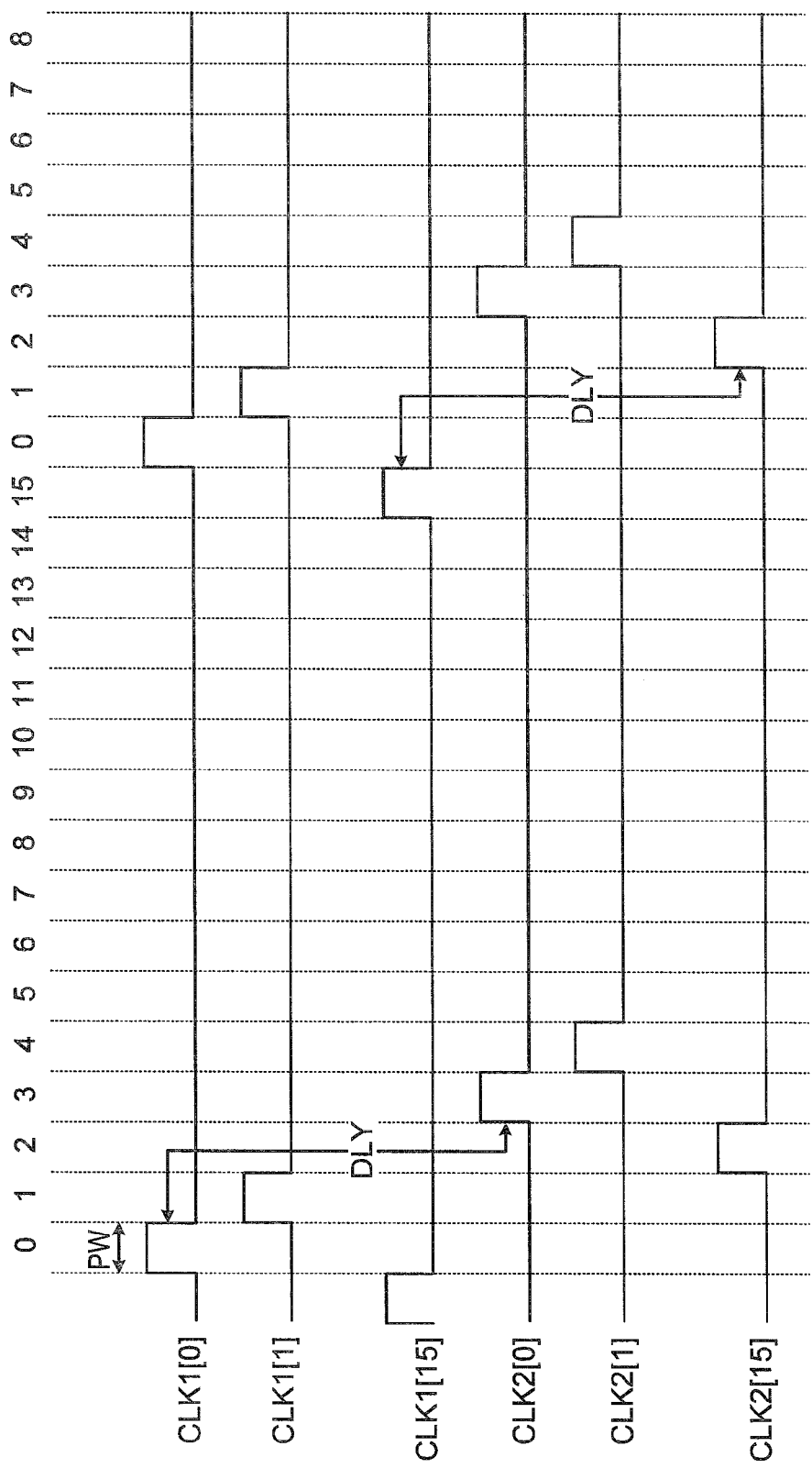
FIG. 10 is a timing diagram showing clock signals applied to an array of electrode driver circuits, in accordance with an embodiment of the present invention.

FIG. 10 is a timing diagram showing clock signals applied to the array of driver circuits 46, in accordance with an embodiment of the present invention. The CLK1[j] and CLK2[j] signals correspond to the clock pulses that are supplied by I2F circuits 66 to the corresponding driver circuits 46, as described above, wherein j is the number of the group (between 0 and 15). These clock pulses, which start and end the active periods of the corresponding driver circuits, are staggered, so that stimulation of the electrodes in each group starts in a different time slot, numbered from 0 to 15 in the figure. This staggered stimulation pattern is useful, inter alia, in maintaining an approximately constant level of electrical power consumption by the circuits of prosthesis 20.

In the example shown in FIG. 10, each group of the electrodes and driver circuits is active over a period of several time slots, from the corresponding CLK1 pulse to the CLK2 pulse that follows it. As a result, the active periods of certain groups overlap. It is desirable, however, that mutually-adjacent electrodes 26 in prosthesis 20 have non-overlapping active periods, so that the adjacent electrodes are available to serve as return electrodes for the active electrodes. This consideration is the reason for the order of interleaving of the different groups of driver circuits 46 that is shown in FIG. 9.

Alternatively, channels 40 may be operated so that the active periods of the different groups of electrodes 26 and driver circuits 46 do not overlap at all, or overlap only minimally.

Dynamic Control of Active Channels

Figure 11:
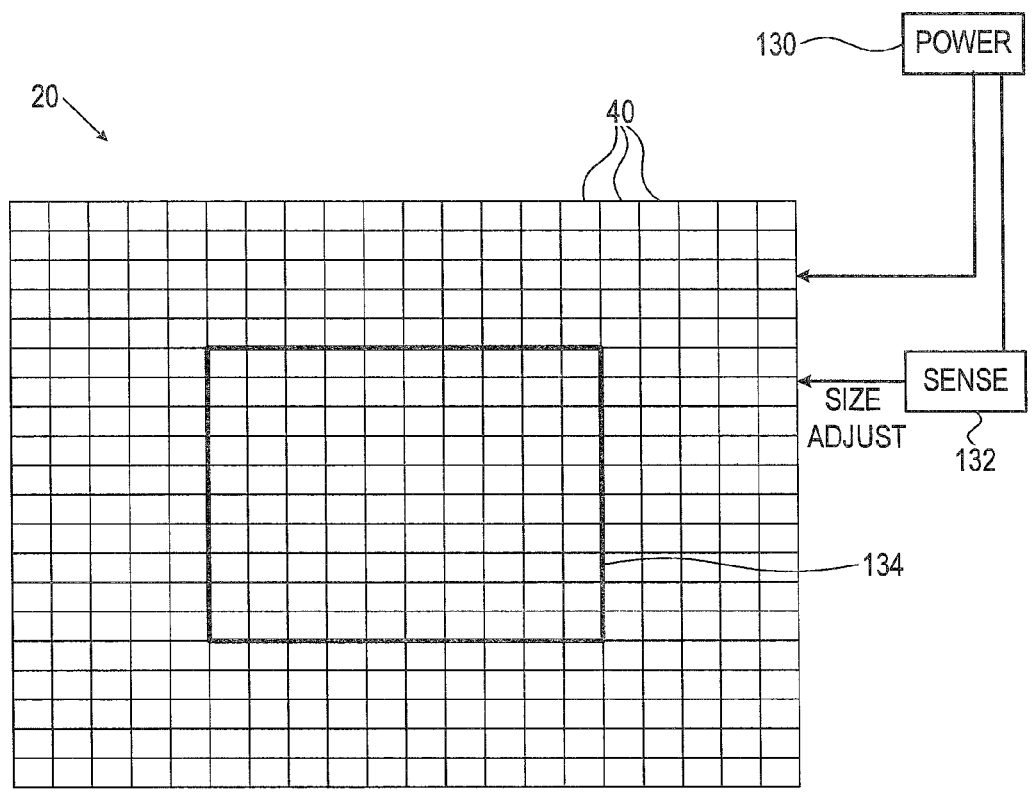
FIG. 11 is a block diagram that schematically illustrates an array of stimulation channels with variable array sizing, in accordance with an embodiment of the present invention.

FIG. 11 is a block diagram that schematically illustrates an array of stimulation channels 40 in retinal prosthesis 20 with variable array sizing, in accordance with an embodiment of the present invention. A power source 130 supplies electrical power to run the circuits of prosthesis 20, as described above. A power sensor 132 monitors the level of power supplied by power source 130, by sensing the output voltage of the power source, for example. As long as the power level is acceptable, full functionality of the entire array of channels 40 is maintained.

When the power available from power source 130 drops, however, the operation of channels 40 may be compromised or may cease altogether. This drop may be transient, due to disruption of power beamed into the eye (as described above), for example, or permanent, due to degradation of components of prosthesis 20 over time. In order to avoid total loss of function, when sensor 132 detects that the power level from source 130 has dropped below a certain level, the sensor automatically reduces the number of active channels 40 (and corresponding electrodes) in the array. Optionally, the sensor may have two or more voltage thresholds, and may reduce the number of active channels further as each threshold is passed.

Although sensor 132 is shown in FIG. 11 as a part of prosthesis 20, in practice the sensor can be implemented either within the implanted prosthesis or outside the human body, such as on a spectacle frame on which power and control circuits for the prosthesis may be mounted. In this latter case, a controller of prosthesis 20, which transmits configuration data to optical interface 56, can reconfigure the set of active channels as required. This capability of activating and deactivating individual channels or groups of channels also enables the channels to be activated one cluster at a time for testing purposes.

In the example shown in FIG. 11, the reduction in the number of active channels is achieved by reducing an active area 134 of prosthesis 20. In this case, only the channels 40 within area 134 receive electrical power and are active in stimulating the corresponding electrodes 26, while the channels outside area 134 are turned off. As a result, the overall power consumption of the prosthesis is reduced, and power source 130 is able to supply sufficient power to the active channels notwithstanding its compromised condition. The field of view of the eye in which the prosthesis is transplanted will be narrowed accordingly. If full power is subsequently restored, sensor 132 may restore all of the channels to active status. The size of area 134 may be controlled dynamically, shrinking gradually smaller or growing larger in proportion to the available power.

Alternatively, other schemes may be used to reduce the number of active channels 40 when the power level drops. The inactive channels may be interleaved in an alternating pattern with the active channels, for example, so that resolution is reduced rather than field of view. For example, in a reduced-power configuration, only alternating channels in alternating rows of the array may be activated. Other such dynamic sizing schemes will be apparent to those skilled in the art and are considered to be within the scope of the present invention.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for neural stimulation, comprising:
providing an array of electrodes for implantation in contact with tissue in an eye of a living subject; and
driving the electrodes in an alternating pattern, so that different groups of the electrodes are driven to stimulate the tissue during different, predetermined respective time periods,
wherein driving the electrodes comprises deactivating a first group of the electrodes when a level of electrical power supplied for driving the electrodes drops below a predetermined threshold, while continuing to provide pulses to a second group of the electrodes.

* * * * *